United States Patent [19]

Armand

[11] Patent Number: 5,494,218

[45] Date of Patent: Feb. 27, 1996

[54] FRAGRANCE DISPENSING TOILET PAPER SPOOL

[76] Inventor: Claude Armand, 6432 Santa Monica Dr., Tampa, Fla. 33615

[21] Appl. No.: 391,526

[22] Filed: Feb. 21, 1995

[51] Int. Cl.$^6$ .................................. A61L 9/12; B65D 1/32
[52] U.S. Cl. .............................. 239/52; 239/327; 242/905
[58] Field of Search ........................ 239/52, 327; 242/905

[56] References Cited

U.S. PATENT DOCUMENTS

| | | | |
|---|---|---|---|
| 3,002,704 | 10/1961 | Grossfeld | 242/905 |
| 3,329,367 | 7/1967 | Paradiso | 242/905 |
| 4,858,831 | 8/1989 | Spector | 239/327 |
| 4,869,407 | 9/1989 | Booth, Jr. et al. | 239/327 |
| 4,912,784 | 4/1990 | Jacobson et al. | 239/327 |
| 4,925,102 | 5/1990 | Jones et al. | 239/52 |

FOREIGN PATENT DOCUMENTS

| | | | |
|---|---|---|---|
| 603596 | 6/1948 | United Kingdom | 239/52 |

Primary Examiner—Karen B. Merritt

[57] ABSTRACT

A spool for rotatably supporting a roll of toilet paper and dispensing fragrance from opposed ends of the spool. The inventive device includes a roll engaging dispensing assembly for positioning within a roll of toilet paper. A pair of mounting assemblies project from opposed ends of the roll engaging dispensing assembly for rotatably supporting the toilet paper relative to a roll holder. The roll engaging dispensing assembly and the associated toilet paper roll can be manually compressed to dispense a fragrance material from opposed ends thereof.

2 Claims, 3 Drawing Sheets

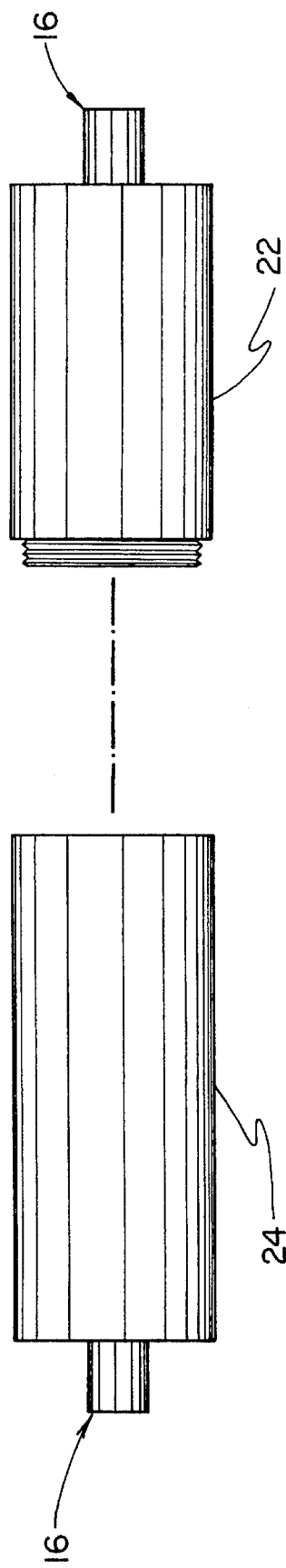
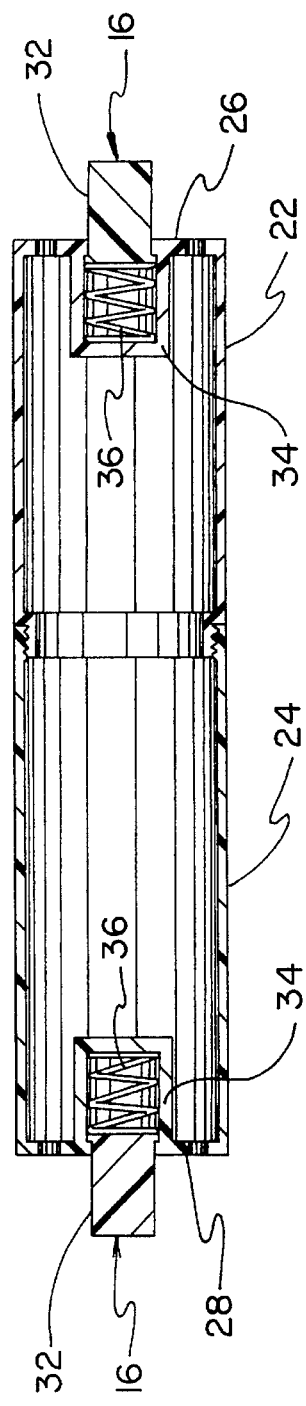
FIG. 4
FIG. 5

FRAGRANCE DISPENSING TOILET PAPER SPOOL

BACKGROUND OF THE INVENTION

1. Field of the Invention

The present invention relates to dispensing devices and more particularly pertains to an fragrance dispensing toilet paper spool for rotatably supporting a roll of toilet paper and dispensing fragrance from opposed ends of the spool.

2. Description of the Prior Art

The use of dispensing devices is known in the prior art. More specifically, dispensing devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art dispensing devices include U.S. Pat. No. 4,044,408; U.S. Pat. No. 4,377,399; U.S. Pat. No. 4,433,441; and U.S. Pat. No. 4,472,841.

While these devices fulfill their respective, particular objectives and requirements, the aforementioned patents do not disclose a fragrance dispensing toilet paper spool for rotatably supporting a roll of toilet paper and dispensing fragrance from opposed ends of the spool which includes a roll engaging dispensing assembly for positioning within a roll of toilet paper, and a pair of mounting assemblies projecting from opposed ends of the roll engaging dispensing assembly for rotatably supporting the toilet paper relative to a roll holder, wherein the roll engaging dispensing assembly and the associated toilet paper roll can be manually compressed to dispense a fragrance material from opposed ends thereof.

In these respects, the fragrance dispensing toilet paper spool according to the present invention substantially departs from the conventional concepts and designs of the prior art, and in so doing provides an apparatus primarily developed for the purpose of rotatably supporting a roll of toilet paper and dispensing fragrance from opposed ends of the spool.

SUMMARY OF THE INVENTION

In view of the foregoing disadvantages inherent in the known types of dispensing devices now present in the prior art, the present invention provides a new fragrance dispensing toilet paper spool construction wherein the same can be utilized for rotatably supporting a roll of toilet paper and dispensing fragrance. As such, the general purpose of the present invention, which will be described subsequently in greater detail, is to provide a new fragrance dispensing toilet paper spool apparatus and method which has many of the advantages of the dispensing devices mentioned heretofore and many novel features that result in a fragrance dispensing toilet paper spool which is not anticipated, rendered obvious, suggested, or even implied by any of the prior art dispensing devices, either alone or in any combination thereof.

To attain this, the present invention generally comprises a spool for rotatably supporting a roll of toilet paper and dispensing fragrance from opposed ends of the spool. The inventive device includes a roll engaging dispensing assembly for positioning within a roll of toilet paper. A pair of mounting assemblies project from opposed ends of the roll engaging dispensing assembly for rotatably supporting the toilet paper relative to a roll holder. The roll engaging dispensing assembly and the associated toilet paper roll can be manually compressed to dispense a fragrance material from opposed ends thereof.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new fragrance dispensing toilet paper spool apparatus and method which has many of the advantages of the dispensing devices mentioned heretofore and many novel features that result in a fragrance dispensing toilet paper spool which is not anticipated, rendered obvious, suggested, or even implied by any of the prior art dispensing devices, either alone or in any combination thereof.

It is another object of the present invention to provide a new fragrance dispensing toilet paper spool which may be easily and efficiently manufactured and marketed.

It is a further object of the present invention to provide a new fragrance dispensing toilet paper spool which is of a durable and reliable construction.

An even further object of the present invention is to provide a new fragrance dispensing toilet paper spool which is susceptible of a low cost of manufacture with regard to both materials and labor, and which accordingly is then susceptible of low prices of sale to the consuming public, thereby making such fragrance dispensing toilet paper spools economically available to the buying public.

Still yet another object of the present invention is to provide a new fragrance dispensing toilet paper spool which provides in the apparatuses and methods of the prior art some of the advantages thereof, while simultaneously overcoming some of the disadvantages normally associated therewith.

3

Still another object of the present invention is to provide a new fragrance dispensing toilet paper spool for rotatably supporting a roll of toilet paper and dispensing fragrance from opposed ends of the spool.

Yet another object of the present invention is to provide a new fragrance dispensing toilet paper spool which includes a roll engaging dispensing assembly for positioning within a roll of toilet paper, and a pair of mounting assemblies from opposed ends of the roll engaging dispensing assembly for rotatably supporting the toilet paper relative to a roll holder, wherein the roll engaging dispensing assembly and the associated toilet paper roll can be manually compressed to dispense a fragrance material from opposed ends thereof.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 4 is an exploded rear elevation view of the invention.

FIG. 5 is a cross sectional view taken along line 5—5 of FIG. 3.

DESCRIPTION OF THE PREFERRED EMBODIMENT

Figure 1:
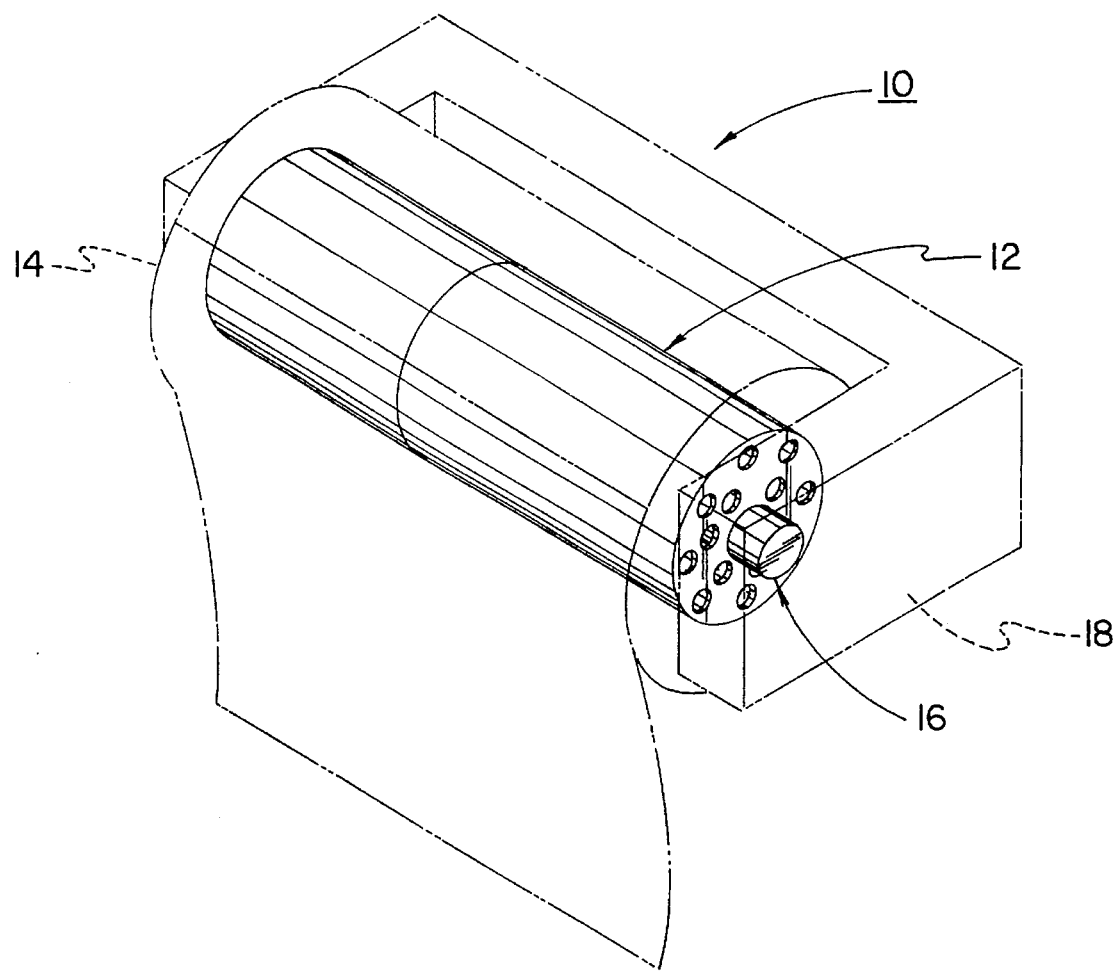
FIG. 1 is an isometric illustration of a fragrance dispensing toilet paper spool according to the present invention in use.
Figure 2:
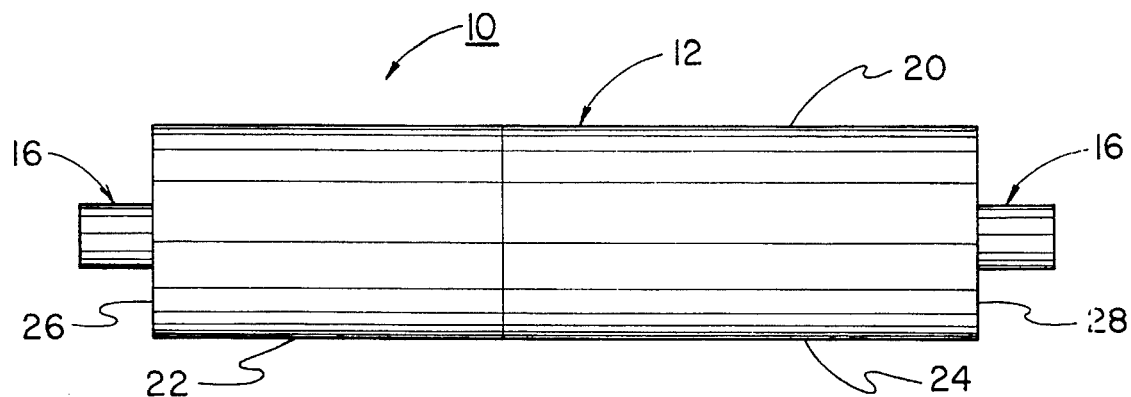
FIG. 2 is a front elevation view thereof.

With reference now to the drawings, and in particular to FIGS. 1–5 thereof, a new fragrance dispensing toilet paper spool embodying the principles and concepts of the present invention and generally designated by the reference numeral 10 will be described.

More specifically, it will be noted that the fragrance dispensing toilet paper spool 10 comprises a roll engaging dispensing means 12 for concentric positioning within a toilet paper roll 14 and for dispensing a fragrance material from opposed ends thereof in response to a mechanical compression of the roll engaging dispensing means 12. A pair of mounting means 16 project from the opposed ends of the roll engaging dispensing means 12 for engaging a toilet paper roll holder 18 to rotatably support the device 10 and associated toilet paper roll 14 relative to the toilet paper roll holder 18. By this structure, toilet paper can be dispensed from the toilet paper roll 14, wherein a resilient compression of the toilet paper roll 14 by an individual will resiliently deform the roll engaging dispensing means 12 to force a fragrance material from opposed ends thereof to freshen an associated room such as a bathroom or the like.

Figure 3:
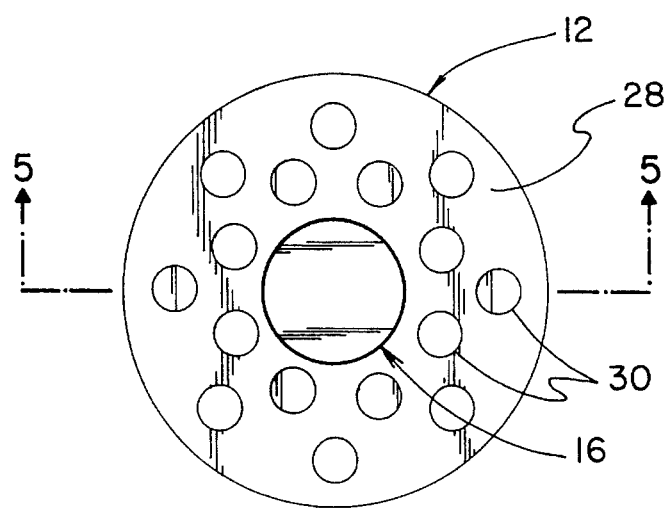
FIG. 3 is a side elevation view of the present invention.

As best illustrated in FIGS. 2 through 5, it can be shown that the roll engaging dispensing means 12 according to the present invention 10 preferably comprises a substantially cylindrical body 20 formed of an unlabeled closed side wall separable into a first portion 22 and a second portion 24. As shown in FIG. 4, an unlabeled threaded annular projection extends from the first portion 22 for threaded engagement with the second portion 24 to permit addition and/or removal of substances within the cylindrical body 20. The cylindrical body 20 further comprises a first circular end wall 26 extending across a first end of the cylindrical side wall thereof, and a second circular end wall 28 extending across a second end of the cylindrical side wall. As shown in FIG. 3 for the second circular end wall 28, the end walls 26 and 28 are shaped so as to define a plurality of through-extending apertures 30 permitting egress of a fragrance material or substance from an interior of the cylindrical body 20. The cylindrical body 20 should be constructed of a substantially resilient material, whereby manual compression thereof will effect pressurized dispensing of a fragrance material, such as granulated fragrance substance or powder, from an interior of the cylindrical 20 through the dispensing apertures 30 of the end walls 26 and 28.

As best illustrated in FIG. 5, it can be shown that each of the mounting means 16 projects from an individual one of the circular end walls 26 or 28 of the cylindrical body 20 for engagement with unlabeled projecting arms of the toilet paper roll holder 18. To this end, each of the mounting means 16 comprises a cylindrical projection 32 slidably mounted within a projection receiver 34. The projection receiver 34 is mounted to an interior surface of the respective end wall 26 or 28 and concentrically positioned over a cylindrical projection aperture directed therethrough. The cylindrical projection 32 is thus received within the projection receiver 34 and supported in an extended position by a spring 36 interposed between the cylindrical projection 32 and the projection receiver 34 so as to force the projection 32 outwardly therefrom as shown in FIG. 5. By this structure, one or both of the cylindrical projections 32 can be biased into the respective projection receiver 34 to facilitate insertion of the device 10 between arms of the toilet paper roll holder 18 as shown in FIG. 1, whereby a releasing of the cylindrical projections 32 will permit projection thereof into opposed apertures of the toilet paper roll holder 18 so as to rotatably support the device 10 relative thereto.

In use, the fragrance dispensing toilet paper spool 10 according to the present invention can be easily utilized to rotatably support a toilet paper roll 14 relative to a toilet paper roll holder 18. A fragrance material such as a powder fragrance material can be positioned within the cylindrical body 20 of the roll engaging dispensing means 12, whereby a manual compression of the toilet paper roll 14 will simultaneous effect compression of the cylindrical body 20 to force the fragrance material therefrom through the dispensing apertures 30 in the respective end walls 26 and 28.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A fragrance dispensing toilet paper spool comprising:

a substantially cylindrical body having a closed side wall separable into a first portion and a second portion; a threaded annular projection extending from the first portion of the cylindrical body and being threadably engaged to the second portion of the cylindrical body to permit selective separation of the portions of the cylindrical body to permit addition and removal of substances within the cylindrical body; a first circular end wall extending across a first end of the cylindrical side wall; and a second circular end wall extending across a second end of the cylindrical side wall, the end walls being shaped so as to define a plurality of through-extending dispensing apertures permitting egress of a fragrance material from an interior of the cylindrical body, wherein the cylindrical body is constructed of a substantially resilient material, whereby manual compression thereof will effect pressurized dispensing of a fragrance material from an interior of the cylindrical body through the dispensing apertures of the end walls, the cylindrical body having a constant diameter along a longitudinal length thereof such that all of an exterior surface of the cylindrical body can be positioned into contact with an interior surface of a toilet paper roll;

a pair of mounting means projecting from opposed ends of the cylindrical body for engaging a toilet paper roll holder to rotatably support the cylindrical body relative to a toilet paper roll holder.

2. The fragrance dispensing toilet paper spool of claim 1, and further comprising a toilet paper roll, with the cylindrical body being positioned within the toilet paper roll such that all of the exterior surface of the cylindrical body is positioned into contact with the interior surface of the toilet paper roll, whereby squeezing of an exterior of the roll will effect compression of the cylindrical body.

* * * * *